US012336856B2

(12) United States Patent
Arakawa

(10) Patent No.: US 12,336,856 B2
(45) Date of Patent: Jun. 24, 2025

(54) STATE ESTIMATION APPARATUS, STATE ESTIMATION METHOD, AND COMPUTER READABLE RECORDING MEDIUM

(71) Applicant: NEC Corporation, Tokyo (JP)

(72) Inventor: Takayuki Arakawa, Tokyo (JP)

(73) Assignee: NEC CORPORATION, Tokyo (JP)

(*) Notice: Subject to any disclaimer, the term of this patent is extended or adjusted under 35 U.S.C. 154(b) by 896 days.

(21) Appl. No.: 17/431,521

(22) PCT Filed: Feb. 28, 2019

(86) PCT No.: PCT/JP2019/007919
§ 371 (c)(1),
(2) Date: Aug. 17, 2021

(87) PCT Pub. No.: WO2020/174681
PCT Pub. Date: Sep. 3, 2020

(65) Prior Publication Data
US 2022/0142605 A1 May 12, 2022

(51) Int. Cl.
A61B 8/08 (2006.01)
A61B 5/00 (2006.01)
(Continued)

(52) U.S. Cl.
CPC ............ A61B 8/08 (2013.01); A61B 5/0816 (2013.01); A61B 5/087 (2013.01); A61B 5/6817 (2013.01)

(58) Field of Classification Search
CPC ....... A61B 5/6817; A61B 5/6815; A61B 8/08; A61B 5/0816; A61B 5/087; A61B 5/0803;
(Continued)

(56) References Cited

U.S. PATENT DOCUMENTS

2012/0001846 A1* 1/2012 Taniguchi ............... G06F 1/163
345/156
2014/0233749 A1* 8/2014 Shimizu ............... H04R 1/1016
381/71.6
(Continued)

FOREIGN PATENT DOCUMENTS

DE 102012219128 A1 * 5/2014 ........... A61B 5/1076
JP 2010-154563 A 7/2010
(Continued)

OTHER PUBLICATIONS

G. A. Pressler, J. P. Mansfield, H. Pasterkamp and G. R. Wodicka, "Detection of respiratory sounds at the external ear," in IEEE Transactions on Biomedical Engineering, vol. 51, No. 12, pp. 2089-2096, Dec. 2004, doi: 10.1109/TBME.2004.836525. (Year: 2004).*
(Continued)

Primary Examiner — Sean D Mattson
Assistant Examiner — Michael Yiming Fang

(57) ABSTRACT

A state estimation apparatus 1 includes: a generation unit 2 configured to generate acoustic characteristic information indicating an acoustic characteristic using a first acoustic signal output to the ear canal and a second acoustic signal produced by the first acoustic signal echoing inside the body; and an estimation unit 3 configured to estimate the state of the vocal tract and the state of the respiratory tract using the acoustic characteristic information.

8 Claims, 8 Drawing Sheets

(51) Int. Cl.
*A61B 5/08* (2006.01)
*A61B 5/087* (2006.01)

(58) Field of Classification Search
CPC ..... A61B 5/4803; A61B 5/4552; A61B 10/00; H04R 1/1016; H04R 1/38
See application file for complete search history.

(56) References Cited

U.S. PATENT DOCUMENTS

| | | |
|---|---|---|
| 2016/0354040 A1 | 12/2016 | Aarts et al. |
| 2017/0086779 A1 | 3/2017 | Kamano et al. |
| 2017/0347180 A1 | 11/2017 | Petrank |
| 2017/0365052 A1 | 12/2017 | Chen et al. |
| 2018/0307818 A1 | 10/2018 | Yano et al. |

FOREIGN PATENT DOCUMENTS

| | | |
|---|---|---|
| JP | 2014-187679 A | 10/2014 |
| JP | 2017-060548 A | 3/2017 |
| JP | 2017-507676 A | 3/2017 |
| JP | 2018-011930 A | 1/2018 |
| WO | 2010/090175 A1 | 8/2010 |
| WO | 2017/069118 A1 | 9/2018 |

OTHER PUBLICATIONS

International Search Report for PCT Application No. PCT/JP2019/007919, mailed on Jun. 4, 2019.

English translation of Written opinion for PCT Application No. PCT/JP2019/007919, mailed on Jun. 4, 2019.

* cited by examiner

Fig.4

| | | | |
|---|---|---|---|
| RESONANT FREQUENCY INFORMATION | | | |
| f1 | | | |
| f2 | | | |
| ⋮ | | | |

41

42

| STATE ESTIMATION INFORMATION | | | |
|---|---|---|---|
| VOCAL TRACT STATE | WHETHER MOUTH IS OPEN OR CLOSED | OPEN | F11 |
| | | | F12 |
| | | | ⋮ |
| | | CLOSED | F21 |
| | | | F22 |
| | | | ⋮ |
| | WHETHER VOCAL CORDS ARE OPEN OR CLOSED | OPEN | F31 |
| | | | F32 |
| | | | ⋮ |
| | | CLOSED | F41 |
| | | | F42 |
| | | | ⋮ |
| | PLACE OF ARTICULATION | a | F51 |
| | | | F52 |
| | | | ⋮ |
| | | e, o | F61 |
| | | | F62 |
| | | | ⋮ |
| | | i | F71 |
| | | | F72 |
| | | | ⋮ |
| | | m, n | F71 |
| | | | F72 |
| | | | ⋮ |
| | | u | F81 |
| | | | F82 |
| | | | ⋮ |
| | | ⋮ | ⋮ |
| RESPIRATORY TRACT STATE | BREATHING TYPE | LUNG BREATHING | F81 |
| | | | F82 |
| | | | ⋮ |
| | | DIAPHRAGMATIC BREATHING | F91 |
| | | | F92 |
| | | | ⋮ |
| | | ⋮ | ⋮ |

Fig.5

| SPECTRAL SHAPE INFORMATION |
|---|
| sp1 |

| STATE ESTIMATION INFORMATION | | | |
|---|---|---|---|
| VOCAL TRACT STATE | WHETHER MOUTH IS OPEN OR CLOSED | OPEN | SP11 |
| | | CLOSED | SP12 |
| | WHETHER VOCAL CORDS ARE OPEN OR CLOSED | OPEN | SP21 |
| | | CLOSED | SP22 |
| | PLACE OF ARTICULATION | a | SP31 |
| | | e, o | SP32 |
| | | i | SP33 |
| | | m, n | SP34 |
| | | u | SP35 |
| | | ⋮ | ⋮ |
| RESPIRATORY TRACT STATE | BREATHING TYPE | LUNG BREATHING | SP41 |
| | | DIAPHRAGMATIC BREATHING | SP42 |
| | | ⋮ | ⋮ |

A

B

STATE ESTIMATION APPARATUS, STATE ESTIMATION METHOD, AND COMPUTER READABLE RECORDING MEDIUM

This application is a National Stage Entry of PCT/JP2019/007919 filed on Feb. 28, 2019, the contents of all of which are incorporated herein by reference, in their entirety.

TECHNICAL FIELD

The present invention relates to a state estimation apparatus and state estimation method for estimating the states of the vocal and respiratory tracts, and further relates to a computer readable recording medium that includes recorded thereon, a program for realizing the state estimation apparatus and state estimation method.

BACKGROUND ART

Techniques for estimating the states of the vocal and respiratory tracts to detect phonation and respiratory abnormalities are known. Such techniques for estimating the states of the vocal and respiratory tracts are useful for carrying out medical and health care smoothly, for example.

As a related technique, Patent Document 1 discloses a system for calculating respiratory tract width using ultrasonic images of transverse sections of the respiratory tract captured using an ultrasonic imaging device, and diagnosing respiratory obstruction using the calculated respiratory tract width.

LIST OF RELATED ART DOCUMENTS

Patent Document

Patent Document 1: Japanese Patent Laid-Open Publication No. 2006-071936 No. 2018-011930

SUMMARY

Technical Problems

However, since ultrasonic images of transverse sections of the respiratory tract are captured using an ultrasonic imaging device or the like in the above-described system disclosed in Patent Document 1, the scale of the system becomes large.

Furthermore, since transverse-section ultrasonic images of the respiratory tract are captured and image processing is performed on the transverse-section ultrasonic images, it takes time to diagnose the state of the respiratory tract.

An example object of the invention is to provide a state estimation apparatus, a state estimation method, and a computer readable recording medium for estimating the states of the vocal and respiratory tracts easily.

Solution to the Problems

In order to achieve the above-described object, a state estimation apparatus according to an example aspect of the invention includes:
at least one memory configured to store instructions; and
at least one processor configured to execute the instructions to:
generate acoustic characteristic information indicating an acoustic characteristic using a first acoustic signal output to the ear canal and a second acoustic signal produced by the first acoustic signal echoing inside the body; and
estimate the state of the vocal tract and the state of the respiratory tract using the acoustic characteristic information.

In addition, in order to achieve the above-described object, a state estimation method according to an example aspect of the invention includes:
generating acoustic characteristic information indicating an acoustic characteristic using a first acoustic signal output to the ear canal and a second acoustic signal produced by the first acoustic signal echoing inside the body; and
estimating the state of the vocal tract and the state of the respiratory tract using the acoustic characteristic information.

Furthermore, in order to achieve the above-described object, a computer readable recording medium that includes a program recorded thereon according to an example aspect of the invention includes recorded thereon, a program including instructions that cause a computer to carry out:
generating acoustic characteristic information indicating an acoustic characteristic using a first acoustic signal output to the ear canal and a second acoustic signal produced by the first acoustic signal echoing inside the body; and
estimating the state of the vocal tract and the state of the respiratory tract using the acoustic characteristic information.

Advantageous Effects of the Invention

As described above, according to the invention, the states of the vocal and respiratory tracts can be estimated easily.

BRIEF DESCRIPTION OF THE DRAWINGS

FIG. 4 is a diagram illustrating one example of data structures of resonant frequency information and state estimation information.
FIG. 5 is a diagram illustrating one example of data structures of spectral shape information and the state estimation information.

EXAMPLE EMBODIMENT

Example Embodiment

Figure 1:
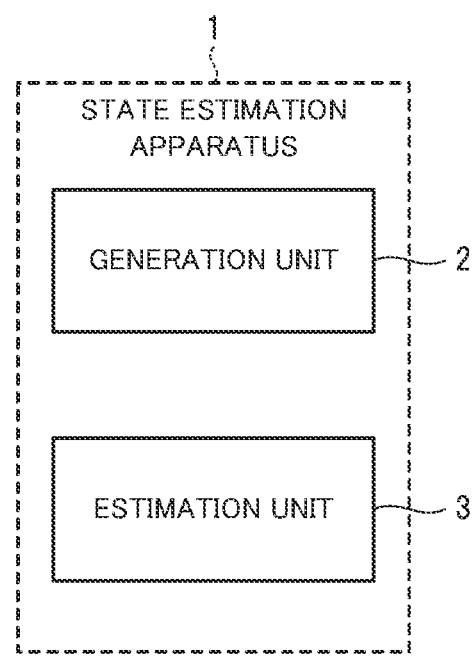
FIG. 1 is a diagram illustrating one example of a state estimation apparatus.

In the following, an example embodiment of the invention will be described with reference to FIGS. 1 to 8.
[Apparatus Configuration]
First, a configuration of a state estimation apparatus 1 in the present example embodiment will be described with reference to FIG. 1. FIG. 1 is a diagram illustrating one example of the state estimation apparatus.

The state estimation apparatus illustrated in FIG. 1 is an apparatus for improving state estimation accuracy. Furthermore, as illustrated in FIG. 1, the state estimation apparatus 1 includes a generation unit 2 and an estimation unit 3.

Of the two units, the generation unit 2 generates acoustic characteristic information indicating an acoustic characteristic using an acoustic signal (first acoustic signal) output to the ear canal and an echo signal (second acoustic signal) produced by the acoustic signal echoing inside the body. The estimation unit 3 estimates the state of the vocal tract and the state of the respiratory tract using the acoustic characteristic information.

In such a manner, in the present example embodiment, acoustic characteristic information such as an impulse response $h(t)$ or a transfer function $H(\omega)$ or $H(z)$ is generated using an acoustic signal $x(t)$ output to the ear canal of a target user and an echo signal $y(t)$ reflecting the states of organs inside the body. Thus, since the states of organs inside the body can be estimated from the acoustic characteristic information, the states of organs can be estimated easily in a short amount of time without the need of a large-scale system as conventionally necessary.

[System Configuration]

Figure 2:
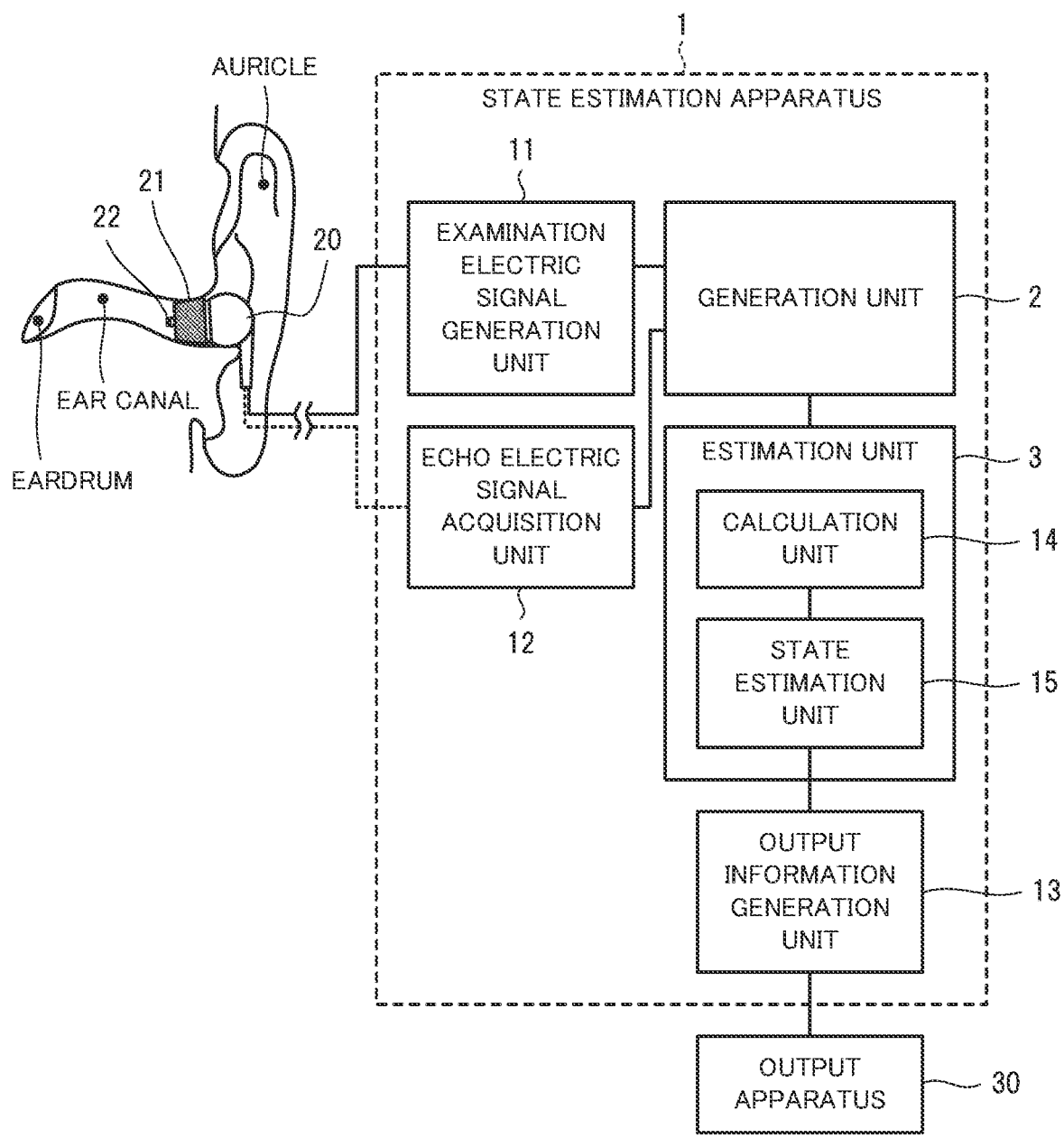
FIG. 2 is a diagram illustrating one example of a system including the state estimation apparatus.

Next, the configuration of the state estimation apparatus 1 in the present example embodiment will be described in detail with reference to FIG. 2. FIG. 2 is a diagram illustrating one example of a system including the state estimation apparatus.

As illustrated in FIG. 2, the system in the present example embodiment includes an ear-mounted apparatus 20 and an output apparatus 30, in addition to the state estimation apparatus 1. Furthermore, the state estimation apparatus 1 includes an examination electric signal generation unit 11, an echo electric signal acquisition unit 12, and an output information generation unit 13, in addition to the generation unit 2 and the estimation unit 3. Furthermore, the estimation unit 3 includes a calculation unit 14 and a state estimation unit 15. The ear-mounted apparatus 20 includes an examination sound signal reproduction unit 21 and an echo sound signal recording unit 22.

The ear-mounted apparatus 20 includes the examination sound signal reproduction unit 21, which is for outputting an acoustic signal to the ear canal, and the echo sound signal recording unit 22, which is for receiving input of (measuring) an echo signal in the ear canal. Specifically, the ear-mounted apparatus 20 is an apparatus that is used in a state in which the ear-mounted apparatus 20 is worn in the ear canal, as illustrated in the cross-sectional diagram of the outer ear (diagram illustrating the auricle, ear canal, and eardrum) in FIG. 2. For example, an earphone provided with a microphone is conceivable as the ear-mounted apparatus 20.

Note that the configuration of the ear-mounted apparatus 20 is not limited to that illustrated in FIG. 2, and any configuration may be adopted as long as an echo signal corresponding to an acoustic signal can be measured.

Upon receiving an electric signal generated by the examination electric signal generation unit 11 that corresponds to an acoustic signal, the examination sound signal reproduction unit 21 (acoustic signal output unit) generates the acoustic signal based on the received electric signal and outputs the generated acoustic signal to the ear canal. Note that a speaker or the like, for example, is conceivable as the examination sound signal reproduction unit 21.

Upon receiving input of an echo signal corresponding to the acoustic signal output from the examination electric signal generation unit 21, the echo sound signal recording unit 22 (acoustic signal input unit) converts the echo signal into an electric signal and transmits the electric signal to the echo electric signal acquisition unit 12. Note that a microphone or the like, for example, is conceivable as the echo sound signal recording unit 22.

The output apparatus 30 acquires the later-described output information, which has been converted into an outputtable format by the output information generation unit 13, and outputs images, sounds, etc., generated based on the output information. The output apparatus 30 is an image display device, etc., in which liquid crystal, organic electroluminescence (EL), or a cathode ray tube (CRT) is used, for example. Furthermore, the image display device may include a sound output device such as a speaker. Note that the output apparatus 30 may be a printing device such as a printer.

The examination electric signal generation unit 11 generates the electric signal used to output the acoustic signal, and transmits the electric signal to the examination sound signal reproduction unit 21. Specifically, the examination electric signal generation unit 11 generates, as the electric signal corresponding to the acoustic signal, a maximal length sequence (M-sequence) signal, a time-stretched pulse (TSP) signal, a Log-TSP signal, or the like. Furthermore, the examination electric signal generation unit 11 transmits the electric signal corresponding to the acoustic signal to the generation unit 2.

Note that a sweep signal, music, audio guidance, etc., may be included in the acoustic signal. Furthermore, the frequencies used for the acoustic signal are set in accordance with target organs. For example, when the vocal and respiratory tracts, etc., are set as targets, the frequency band of the acoustic signal is preferably set to 100-4 k [Hz]. However, there is no limitation to this frequency band.

Here, the vocal tract (articulatory organs), for example, is a path of voice, and is a cavity in the body through which sound produced by the vocal cords passes before being emitted to the outside of the body. The respiratory tract (phonatory organs), for example, is a path of respiratory sound and is involved in external respiration. The respiratory tract is formed from the upper respiratory tract (the nasal cavity, the pharynx, the larynx, etc.) and the lower respiratory tract (the trachea, the primary bronchi, the lungs, etc.).

The echo electric signal acquisition unit 12 receives the electric signal corresponding to the echo signal from the echo sound signal recording unit 22, adjusts the received electric signal, and transmits the adjusted electric signal to the generation unit 2. Specifically, the echo electric signal acquisition unit 12 adjusts the received electric signal using a circuit including a filter, an amplifier, etc., and transmits the adjusted electric signal to the generation unit 2.

The generation unit 2 generates acoustic characteristic information indicating an acoustic characteristic using an electric signal corresponding to an acoustic signal $x(t)$ and an electric signal corresponding to an echo signal $y(t)$. For example, an impulse response $h(t)$, a transfer function $H(\omega)$ or $H(z)$ obtained by performing Fourier transform or Laplace transform on the impulse response, or the like is used as the acoustic characteristic.

Specifically, the generation unit 2 first receives the electric signal corresponding to the acoustic signal $x(t)$ from the examination electric signal generation unit 11. Furthermore, the generation unit 2 receives the electric signal corresponding to the echo signal $y(t)$ from the echo electric signal acquisition unit 12. Subsequently, the generation unit 2 generates the acoustic characteristic information (an impulse response h(t), a transfer function H(ω) or H(z), or the like) based on the received electric signals corresponding to the acoustic signal x(t) and the echo signal y(t).

Subsequently, the generation unit 2 stores the acoustic characteristic information to a storage unit, which is not illustrated. Note that the storage unit may be provided inside or outside the state estimation apparatus 1.

Since the echo signal y(t) reflects changes (changes in reflection ratio, attenuation rate, etc.) that are in accordance with the states of the subject's organs, information relating to the states of organs inside the body can be extracted by generating the acoustic characteristic information, which is an impulse response h(t), a transfer function H(ω) or H(z), or the like. Note that the reflection ratio is the ratio of the reflection to the input, and the attenuation rate is the rate of attenuation per unit time or unit cycle.

Note that the echo signal includes acoustic signals coming back from spaces (the ear canal, and the vocal and respiratory tracts) located between the head and the lungs, for example.

The estimation unit 3 estimates states using the acoustic characteristic information. Specifically, the estimation unit 3 estimates the state of the vocal tract and the state of the respiratory tract using the acoustic characteristic information. Note that the estimation unit 3 estimates at least one or more states among whether the mouth is open or closed, whether the vocal cords are open or closed, the place of articulation, and breathing type (lung breathing, diaphragmatic breathing, etc.), and sets the states as the state of the vocal tract and the state of the respiratory tract.

The estimation unit 3 (the calculation unit 14 and the state estimation unit 15) will be described in detail.

Using the acoustic characteristic information, the calculation unit 14 calculates resonant frequency information including information indicating resonant frequencies (frequencies with peak values in frequency characteristics), or spectral shape information indicating a spectral shape.

Figure 3:
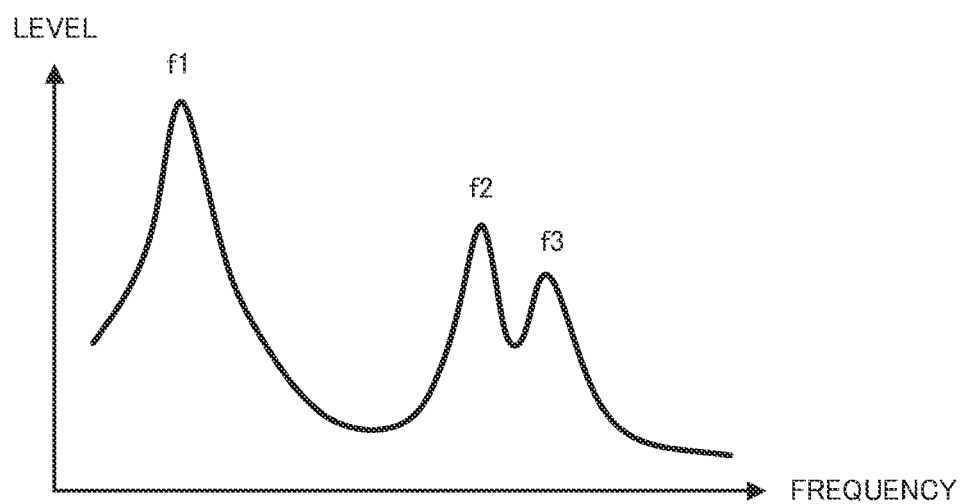
FIG. 3 is a diagram illustrating one example of resonant frequencies and a spectral shape.

FIG. 3 is a diagram illustrating one example of resonant frequencies and a spectral shape. FIG. 3 illustrates resonant frequencies f1, f2, and f3 included in resonant frequency information, and a spectral shape included in spectral shape information.

The calculation of resonant frequencies will be described.

The calculation unit 14 first acquires the acoustic characteristic information from the generation unit 2. Subsequently, the calculation unit 14 performs spectral analysis using the acoustic characteristic, and calculates resonant frequencies for the subject. The calculation unit 14 calculates resonant frequencies using linear predictive coding (LPC), etc., as the spectral analysis, for example. Then, the calculation unit 14 generates resonant frequency information indicating the resonant frequencies, and stores the generated resonant frequency information to the storage unit. Note that the method for calculating resonant frequencies is not limited to LPC, and any method may be used as long as resonant frequencies can be calculated.

The calculation of a spectral shape will be described.

The calculation unit 14 first acquires the acoustic characteristic information from the generation unit 2. Subsequently, the calculation unit 14 performs spectral analysis using the acoustic characteristic, and calculates a spectral shape (spectral envelope) for the subject. The calculation unit 14 calculates a spectral shape using cepstrum analysis, etc., as the spectral analysis, for example. Then, the calculation unit 14 generates spectral shape information indicating the spectral shape, and stores the generated spectral shape information to the storage unit.

The state estimation unit 15 estimates the states of the subject's organs using the generated resonant frequency information or spectral shape information. Specifically, the state estimation unit 15 first acquires the generated resonant frequency information or spectral shape information.

Subsequently, the state estimation unit 15 estimates the states of the subject's organs by using the resonant frequency information or spectral shape information and referring to state estimation information stored in advance. For example, the states of organs are the state of the vocal tract, the state of the respiratory tract, etc.

Note that, as the state of the vocal tract, states such as whether the mouth is open or closed, whether the vocal cords are open or closed, and the place of articulation are conceivable, for example. As the state of the respiratory tract, breathing type is conceivable, for example.

In regard to whether the mouth is open or closed, if the mouth is open, the sound pressure at low frequencies decreases since the pressure inside the mouth decreases. Furthermore, when the mouth is opened and closed, resonant frequencies change since the open and closed ends in the air column resonance model change.

In regard to whether the vocal cords are open or closed, the air column length changes when the vocal cords (glottis) are opened and closed. For example, the air column length from the mouth to the vocal cords or the air column length from the mouth to the lungs changes.

In regard to the place of articulation, the spectral shape and the formant frequencies including the resonant frequencies change when the positions of the tongue and teeth change.

In regard to breathing type, the size of the respiratory tract changes depending upon whether lung breathing (the lungs contract) or diaphragmatic breathing (the diaphragm moves up and down) is being performed.

Subsequently, the state estimation unit 15 generates state information indicating the states of the organs, and stores the state information to the storage unit. Furthermore, the state estimation unit 15 transmits the information indicating the estimated states of the organs to the output information generation unit 13.

For example, the state information includes information indicating the state of the vocal tract and the state of the respiratory tract. For example, the state of the vocal tract includes information indicating states such as whether the mouth is open or closed, whether the vocal cords are open or closed, the place of articulation, etc. Furthermore, the state of the respiratory tract includes information indicating breathing type, for example.

A case in which resonant frequencies are used will be described.

The state estimation unit 15 first acquires the resonant frequency information generated by the calculation unit 14. Subsequently, the state estimation unit 15 calculates distances using the resonant frequency information and the state estimation information illustrated in FIG. 4, and estimates the states of the organs using the calculated distances.

FIG. 4 is a diagram illustrating one example of data structures of the resonant frequency information and the state estimation information. For example, in a case in which the state estimation unit 15 estimates whether the mouth is open or closed, the state estimation unit 15 uses a feature amount characterized by resonant frequencies f1, f2, . . . included in resonant frequency information 41 and calculates the distance to a feature amount characterized by resonant frequencies F11, F12, . . . corresponding to "OPEN" included in "WHETHER MOUTH IS OPEN OR CLOSED" included in state estimation information 42 and the distance to a feature amount characterized by resonant frequencies F21, F22, . . . corresponding to "CLOSED" included in "WHETHER MOUTH IS OPEN OR CLOSED" included in the state estimation information 42.

Furthermore, the state estimation unit 15 selects the closer one of the feature amounts and sets the state corresponding to the selected feature amount as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit.

A case in which spectral shapes are used will be described.

The state estimation unit 15 first acquires the spectral shape information generated by the calculation unit 14. Subsequently, the state estimation unit 15 calculates distances using the spectral shape information and the state estimation information illustrated in FIG. 5, and estimates the states of the organs using the calculated distances.

FIG. 5 is a diagram illustrating one example of data structures of the spectral shape information and the state estimation information. For example, in a case in which the state estimation unit 15 estimates whether the mouth is open or closed, the state estimation unit 15 uses a feature amount characterized by information sp1 indicating a spectral shape included in spectral shape information 51 and calculates the distance to a feature amount characterized by a spectral shape SP11 corresponding to "OPEN" included in "WHETHER MOUTH IS OPEN OR CLOSED" included in state estimation information 52 and the distance to a feature amount characterized by a spectral shape SP12 corresponding to "CLOSED" included in "WHETHER MOUTH IS OPEN OR CLOSED" included in the state estimation information 52.

Figure 6:
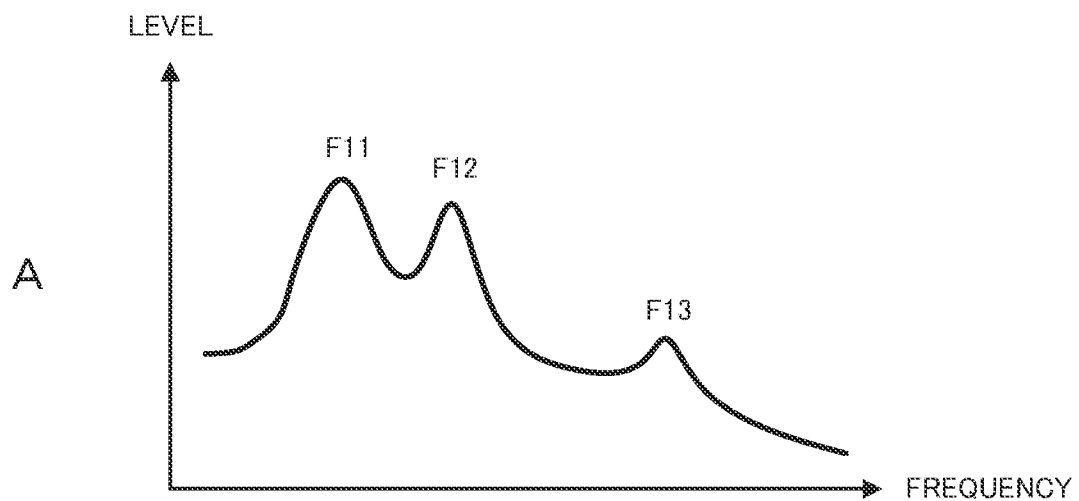
FIG. 6 is a diagram illustrating one example of resonant frequencies and spectral shapes included in the state estimation information.
Figure 6:
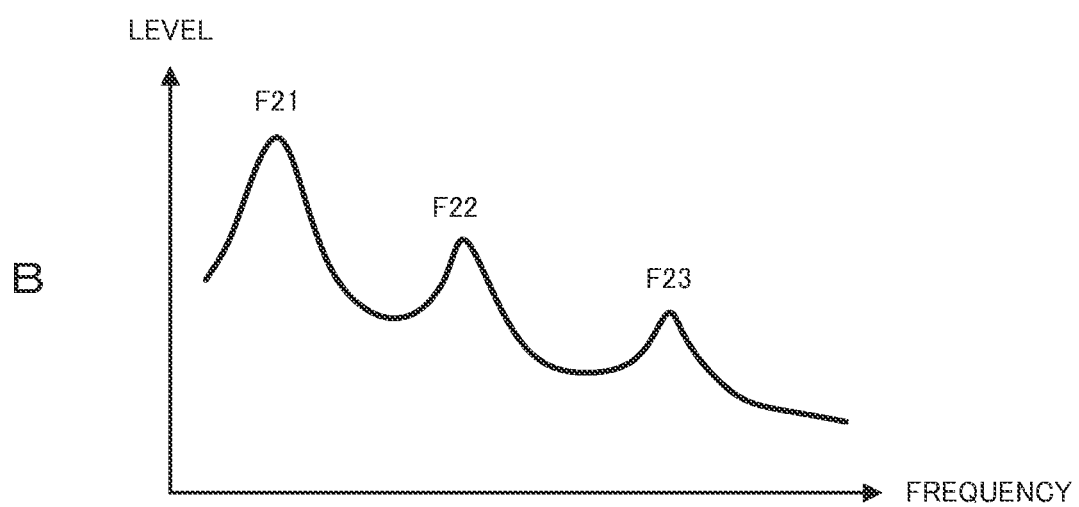

FIG. 6 is a diagram illustrating one example of resonant frequencies and spectral shapes included in the state estimation information. The spectral shapes shown in portions A and B of FIG. 6 correspond to the spectral shapes SP11 and SP12 illustrated in FIG. 5, for example.

Then, the state estimation unit 15 selects the state corresponding to the closer one of the feature amounts and sets the state as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit.

Upon acquiring the information indicating the states of the organs from the state estimation unit 15, the output information generation unit 13 generates output information based on the information and transmits the output information to the output apparatus 30. The output apparatus 30 outputs the state of the subject based on the output information.

[Apparatus Operations]

Figure 7:
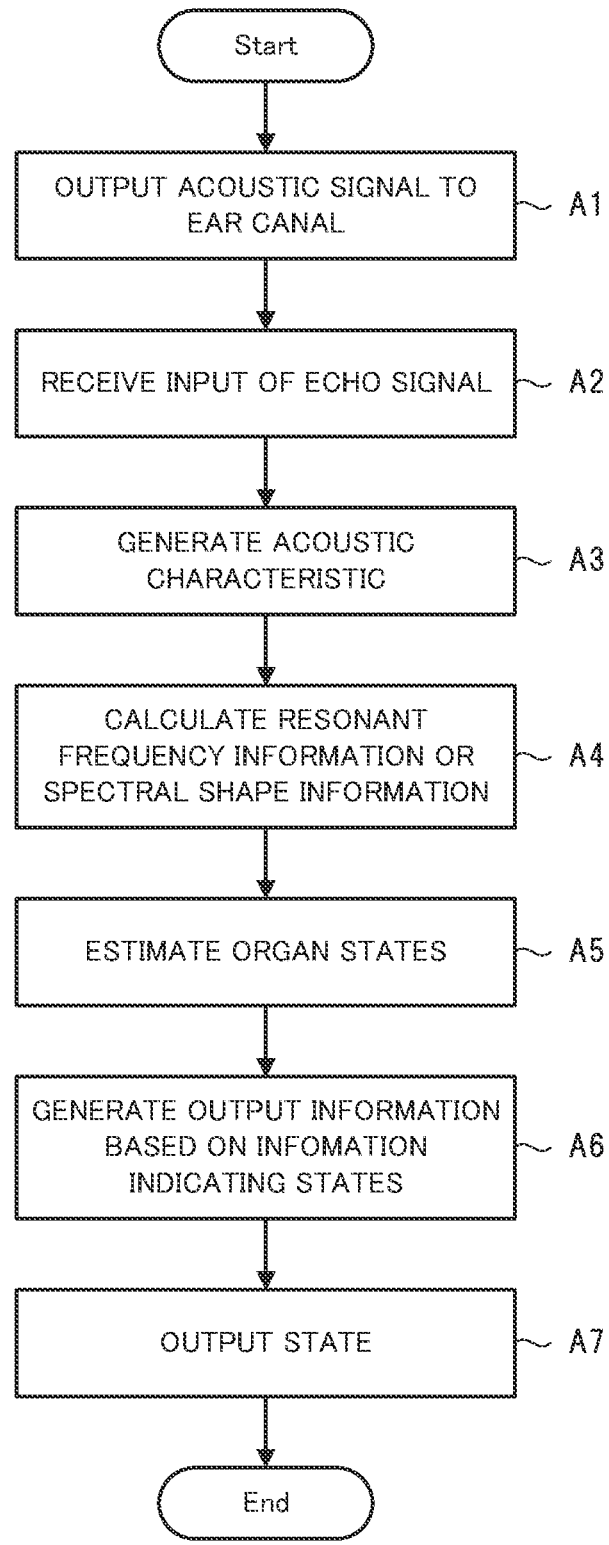
FIG. 7 is a diagram illustrating one example of operations of the state estimation apparatus.

Next, operations of the state estimation apparatus in the example embodiment of the invention will be described with reference to FIG. 7. FIG. 7 is a diagram illustrating one example of operations of the state estimation apparatus. FIGS. 2 to 6 will be referred to as needed in the following description. Furthermore, in the present example embodiment, a state estimation method is implemented by causing the state estimation apparatus to operate. Accordingly, the following description of the operations of the state estimation apparatus is substituted for the description of the state estimation method in the present example embodiment.

As illustrated in FIG. 7, first, upon receiving an electric signal that corresponds to an acoustic signal and that is generated by the examination electric signal generation unit 11, the examination sound signal reproduction unit 21 generates the acoustic signal based on the received electric signal and outputs the generated acoustic signal to the ear canal (step A1).

Subsequently, the echo sound signal recording unit 22 receives input of (measures) an echo signal corresponding to the acoustic signal output from the examination electric signal generation unit 21 (step A2). Then, the echo sound signal recording unit 22 converts the received echo signal into an electric signal and transmits the electric signal to the echo electric signal acquisition unit 12.

Subsequently, the generation unit 2 generates acoustic characteristic information indicating an acoustic characteristic using the electric signal corresponding to the acoustic signal x(t) and the electric signal corresponding to the echo signal y(t) (step A3). For example, an impulse response h(t), a transfer function H($\omega$) or H(z) obtained by performing Fourier transform or Laplace transform on the impulse response, or the like is used as the acoustic characteristic.

Specifically, in step A3, the generation unit 2 first receives the electric signal corresponding to the acoustic signal x(t) from the examination electric signal generation unit 11. Furthermore, the generation unit 2 receives the electric signal corresponding to the echo signal y(t) from the echo electric signal acquisition unit 12.

Subsequently, in step A3, the generation unit 2 generates the acoustic characteristic information (an impulse response h(t), a transfer function H($\omega$) or H(z), or the like) based on the received electric signals corresponding to the acoustic signal x(t) and the echo signal y(t). Furthermore, in step A3, the generation unit 2 stores the acoustic characteristic information to the storage unit, which is not illustrated.

Subsequently, the calculation unit 14 calculates resonant frequency information including information indicating resonant frequencies or spectral shape information indicating a spectral shape using the acoustic characteristic information (step A4).

The calculation of resonant frequencies in step A4 will be described.

In step A4, the calculation unit 14 first acquires the acoustic characteristic information from the generation unit 2. Subsequently, the calculation unit 14 performs spectral analysis using the acoustic characteristic, and calculates resonant frequencies for the subject. The calculation unit 14 calculates resonant frequencies using linear predictive coding (LPC), etc., as the spectral analysis, for example. Then, in step A4, the calculation unit 14 generates resonant frequency information indicating the resonant frequencies, and stores the generated resonant frequency information to the storage unit.

The calculation of a spectral shape in step A4 will be described.

In step A4, the calculation unit 14 first acquires the acoustic characteristic information from the generation unit 2. Subsequently, the calculation unit 14 performs spectral analysis using the acoustic characteristic, and calculates a spectral shape (spectral envelope) for the subject. The calculation unit 14 calculates a spectral shape using cepstrum analysis, etc., as the spectral analysis, for example. Then, in step A4, the calculation unit 14 generates spectral shape information indicating the spectral shape, and stores the generated spectral shape information to the storage unit.

Subsequently, the state estimation unit 15 estimates the states of the subject's organs using the generated resonant frequency information or spectral shape information (step A5). Specifically, in step A5, the state estimation unit 15 first acquires the generated resonant frequency information or spectral shape information.

Subsequently, in step A5, the state estimation unit 15 estimates the states of the subject's organs by referring to state estimation information stored in advance by using the resonant frequency information or spectral shape information.

Subsequently, in step A5, the state estimation unit 15 generates state information indicating the states of the organs, and stores the state information to the storage unit. For example, the state information includes information indicating the state of the vocal tract and the state of the respiratory tract. For example, the state of the vocal tract includes information indicating states such as whether the mouth is open or closed, whether the vocal cords are open or closed, the place of articulation, etc. Furthermore, the state of the respiratory tract includes information indicating breathing type, for example.

A case in which resonant frequencies are used in step A5 will be described.

In step A5, the state estimation unit 15 first acquires the resonant frequency information generated by the calculation unit 14. Subsequently, the state estimation unit 15 calculates distances using the resonant frequency information and the state estimation information illustrated in FIG. 4, and estimates the states of the organs using the calculated distances.

For example, in a case in which the state estimation unit 15 estimates whether the mouth is open or closed, the state estimation unit 15 uses a feature amount characterized by resonant frequencies f1, f2, . . . included in resonant frequency information 41 and calculates the distance to a feature amount characterized by resonant frequencies F11, F12, . . . corresponding to "OPEN" included in "WHETHER MOUTH IS OPEN OR CLOSED" included in state estimation information 42 and the distance to a feature amount characterized by resonant frequencies F21, F22, . . . corresponding to "CLOSED" included in "WHETHER MOUTH IS OPEN OR CLOSED" included in the state estimation information 42.

Then, in step A5 the state estimation unit 15 selects the closer one of the feature amounts and sets the state corresponding to the selected feature amount as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit.

A case in which a spectral shape is used in step A5 will be described.

In step A5, the state estimation unit 15 first acquires the spectral shape information generated by the calculation unit 14. Subsequently, in step A5, the state estimation unit 15 calculates distances using the spectral shape information and the state estimation information illustrated in FIG. 5, and estimates the states of the organs using the calculated distances.

For example, in a case in which the state estimation unit 15 estimates whether the mouth is open or closed, the state estimation unit 15 uses a feature amount characterized by information sp1 indicating a spectral shape included in spectral shape information 51 and calculates the distance to a feature amount characterized by a spectral shape SP11 corresponding to "OPEN" included in "WHETHER MOUTH IS OPEN OR CLOSED" included in state estimation information 52 and the distance to a feature amount characterized by a spectral shape SP12 corresponding to "CLOSED" included in "WHETHER MOUTH IS OPEN OR CLOSED" included in the state estimation information 52.

Then, in step A5, the state estimation unit 15 selects the state corresponding to the closer one of the feature amounts and sets the state as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit. Furthermore, in step A5, the state estimation unit 15 transmits the information indicating the estimated states to the output information generation unit 13.

Subsequently, upon acquiring the information indicating the states from the state estimation unit 15, the output information generation unit 13 generates output information based on the information (step A6). Furthermore, the output information generation unit 13 transmits the output information to the output apparatus 30. Subsequently, the output apparatus 30 outputs the state of the subject based on the output information (step A7).

Effects of Example Embodiment

As described above, according to the present example embodiment, acoustic characteristic information such as an impulse response h(t) or a transfer function H(z) is generated using an acoustic signal x(t) output to the ear canal of a target user and an echo signal y(t) reflecting the states of organs inside the body. Thus, the states of organs can be estimated easily in a short amount of time without the need of a large-scale system as conventionally necessary.

Furthermore, by using the present example embodiment, states of organs can be promptly estimated, and thus abnormalities in phonation, breathing, etc., of a subject can be discovered promptly. Accordingly, application is possible to voice profiling, etc., in fields such as criminal investigation, marketing, and medical and health care.

[Program]

It suffices for a program in the example embodiment of the invention to be a program that causes a computer to carry out steps A1 to A7 illustrated in FIG. 7. By installing this program on a computer and executing the program, the state estimation apparatus and the state estimation method in the present example embodiment can be realized. In this case, the processor of the computer functions and performs processing as the generation unit 2, the estimation unit 3 (the calculation unit 14 and the state estimation unit 15), and the output information generation unit 13.

Furthermore, the program in the present example embodiment may be executed by a computer system formed from a plurality of computers. In this case, the computers may each function as one of the generation unit 2, the estimation unit 3 (the calculation unit 14 and the state estimation unit 15), and the output information generation unit 13, for example.

[Physical Configuration]

Figure 8:
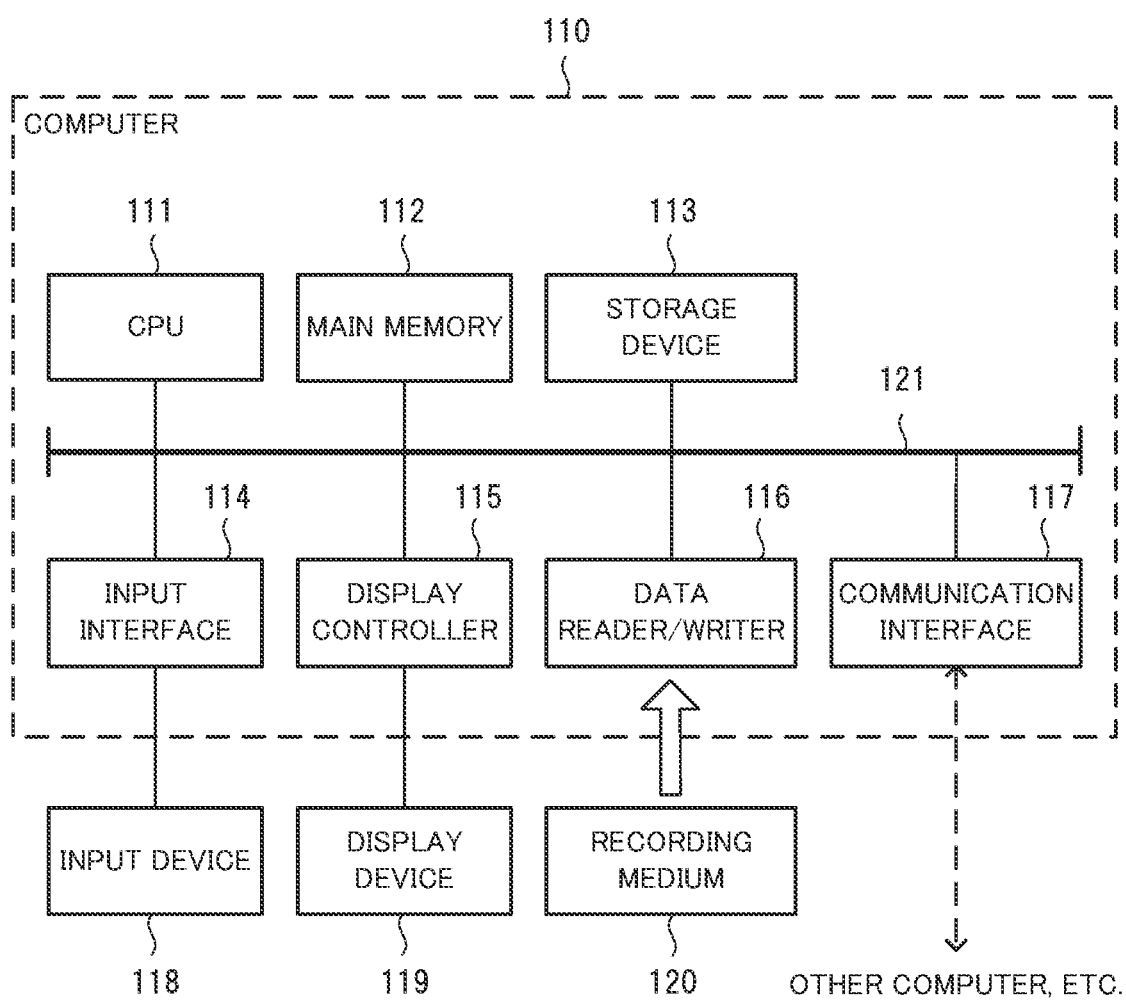
FIG. 8 is a diagram illustrating one example of a computer for realizing the state estimation apparatus.

Here, a computer that realizes the state estimation apparatus by executing the program in the example embodiment will be described with reference to FIG. 8. FIG. 8 is a block diagram illustrating one example of a computer realizing the state estimation apparatus in the example embodiment of the invention.

As illustrated in FIG. 8, a computer 110 includes a CPU 111, a main memory 112, a storage device 113, an input interface 114, a display controller 115, a data reader/writer 116, and a communication interface 117. These components are connected via a bus 121 so as to be capable of performing data communication with one another. Note that the computer 110 may include a graphics processing unit (GPU) or a field-programmable gate array (FPGA) in addition to the CPU 111 or in place of the CPU 111.

The CPU 111 loads the program (codes) in the present example embodiment, which is stored in the storage device 113, onto the main memory 112, and performs various computations by executing these codes in a predetermined order. The main memory 112 is typically a volatile storage device such as a dynamic random access memory (DRAM). Furthermore, the program in the present example embodiment is provided in a state such that the program is stored in a computer readable recording medium 120. Note that the program in the present example embodiment may also be a program that is distributed on the Internet, to which the computer 110 is connected via the communication interface 117.

In addition, specific examples of the storage device 113 include semiconductor storage devices such as a flash memory, in addition to hard disk drives. The input interface 114 mediates data transmission between the CPU 111 and input equipment 118 such as a keyboard and a mouse. The display controller 115 is connected to a display device 119, and controls the display performed by the display device 119.

The data reader/writer 116 mediates data transmission between the CPU 111 and the recording medium 120, and executes the reading out of the program from the recording medium 120 and the writing of results of processing in the computer 110 to the recording medium 120. The communication interface 117 mediates data transmission between the CPU 111 and other computers.

Furthermore, specific examples of the recording medium 120 include a general-purpose semiconductor storage device such as a CompactFlash (registered trademark, CF) card or a Secure Digital (SD) card, a magnetic recording medium such as a flexible disk, and an optical recording medium such as a compact disk read-only memory (CD-ROM).

Note that the state estimation apparatus 1 in the present example embodiment can also be realized by using pieces of hardware corresponding to the respective units, rather than using a computer on which the program is installed. Furthermore, a portion of the state estimation apparatus 1 may be realized by using a program, and the remaining portion of the state estimation apparatus 1 may be realized by using hardware.

[Supplementary Note]

In relation to the above example embodiment, the following Supplementary notes are further disclosed. While a part of or the entirety of the above-described example embodiment can be expressed by Supplementary note 1) to (Supplementary note 10) described in the following, the invention is not limited to the following description.

(Supplementary Note 1)

A state estimation apparatus including:
 a generation unit configured to generate acoustic characteristic information indicating an acoustic characteristic using a first acoustic signal output to the ear canal and a second acoustic signal produced by the first acoustic signal echoing inside the body; and
 an estimation unit configured to estimate the state of the vocal tract and the state of the respiratory tract using the acoustic characteristic information.

(Supplementary Note 2)

The state estimation apparatus according to Supplementary note 1, wherein
 the estimation unit estimates at least one or more states among whether the mouth is open or closed, whether the vocal cords are open or closed, the place of articulation, and breathing type, and sets the states as the state of the vocal tract and the state of the respiratory tract.

(Supplementary Note 3)

The state estimation apparatus according to Supplementary note 1 or 2, wherein
 the estimation unit generates resonant frequency information indicating resonant frequencies or spectral shape information indicating a spectral shape using the acoustic characteristic information, and estimates the state of the vocal tract and the state of the respiratory tract using the generated resonant frequency information or spectral shape information.

(Supplementary Note 4)

The state estimation apparatus according to any one of Supplementary notes 1 to 3, further comprising:
 an acoustic signal output unit configured to output the first acoustic signal to the ear canal; and
 an acoustic signal input unit configured to receive input of the second acoustic signal.

(Supplementary Note 5)

A state estimation method including:
 (a) a step of generating acoustic characteristic information indicating an acoustic characteristic using a first acoustic signal output to the ear canal and a second acoustic signal produced by the first acoustic signal echoing inside the body; and
 (b) a step of estimating the state of the vocal tract and the state of the respiratory tract using the acoustic characteristic information.

(Supplementary Note 6)

The state estimation method according to Supplementary note 5, wherein
 in the (b) step, at least one or more states among whether the mouth is open or closed, whether the vocal cords are open or closed, the place of articulation, and breathing type are estimated and set as the state of the vocal tract and the state of the respiratory tract.

(Supplementary Note 7)

The state estimation method according to Supplementary note 5 or 6, wherein
 in the (b) step, resonant frequency information indicating resonant frequencies or spectral shape information indicating a spectral shape is generated using the acoustic characteristic information, and the state of the vocal tract and the state of the respiratory tract are estimated using the generated resonant frequency information or spectral shape information.

(Supplementary Note 8)

A computer readable recording medium that includes recorded thereon, a program including instructions that cause a computer to carry out:
(a) a step of generating acoustic characteristic information indicating an acoustic characteristic using a first acoustic signal output to the ear canal and a second acoustic signal produced by the first acoustic signal echoing inside the body; and
(b) a step of estimating the state of the vocal tract and the state of the respiratory tract using the acoustic characteristic information.

(Supplementary Note 9)

The computer readable recording medium according to Supplementary note 8, wherein
in the (b) step, at least one or more states among whether the mouth is open or closed, whether the vocal cords are open or closed, the place of articulation, and breathing type are estimated and set as the state of the vocal tract and the state of the respiratory tract.

(Supplementary Note 10)

The computer readable recording medium according to Supplementary note 8 or 9, wherein
in the (b) step, resonant frequency information indicating resonant frequencies or spectral shape information indicating a spectral shape is generated using the acoustic characteristic information, and the state of the vocal tract and the state of the respiratory tract are estimated using the generated resonant frequency information or spectral shape information.

The invention has been described with reference to an example embodiment above, but the invention is not limited to the above-described example embodiment. Within the scope of the invention, various changes that could be understood by a person skilled in the art could be applied to the configurations and details of the invention.

INDUSTRIAL APPLICABILITY

As described above, according to the invention, the states of the vocal and respiratory tracts can be estimated easily. The invention is useful in fields in which voice profiling, etc., need to be performed. Specifically, the invention is useful in fields such as criminal investigation, marketing, and medical and health care.

REFERENCE SIGNS LIST

1 State estimation apparatus
2 Generation unit
3 Estimation unit
11 Examination electric signal generation unit
12 Echo electric signal acquisition unit
13 Output information generation unit
14 Calculation unit
15 State estimation unit
20 Ear-mounted apparatus
21 Examination sound signal reproduction unit
22 Echo sound signal recording unit
30 Output apparatus
41 Resonant frequency information
42 State estimation information
51 Spectral shape information
52 State estimation information
110 Computer
111 CPU
112 Main memory
113 Storage device
114 Input interface
115 Display controller
116 Data reader/writer
117 Communication interface
118 Input equipment
119 Display device
120 Recording medium
121 Bus

What is claimed is:

1. A system comprising:
an ear-mounted apparatus at least partially insertable into an ear canal of a body and comprising:
a speaker to output a first acoustic signal into the ear canal of the body; and
a microphone to detect a second acoustic signal produced by the first acoustic signal echoing inside the body; and
a state estimation apparatus comprising:
at least one memory storing instructions; and
at least one processor configured to execute the instructions to:
generate acoustic characteristic information indicating an acoustic characteristic, using the first acoustic signal output to an ear canal of a body and the second acoustic signal produced by the first acoustic signal echoing inside the body;
generate resonant frequency information indicating resonant frequencies, or spectral shape information indicating a spectral shape, using the acoustic characteristic information; and
estimate a state of a vocal tract of the body and a state of a respiratory tract of the body, using the generated resonant frequency information or spectral shape information, wherein each of the state of the vocal tract and the state of the respiratory tract is any one or any one or more of:
a state indicating whether a mouth of the body is open or closed,
a state indicating whether vocal cords of the body are open or closed,
a state indicating a place of articulation of a tongue of the body, and
a state indicating a type of breathing of the body.

2. The state estimation apparatus according to claim 1, wherein the at least processor is configured to execute the instructions to:
output the first acoustic signal to the speaker to output to the ear canal; and
input the second acoustic signal detected by the microphone.

3. The system according to claim 1, wherein the ear-mounted apparatus further comprises an outer portion that, when the ear-mounted apparatus is inserted into the ear canal, is configured to remain at least partially outside the ear canal and is accessible from an ear auricle of the body.

4. The system according to claim 3, wherein the speaker is adjacent to the outer portion, and is configured to be insertable into the ear canal in that a perimeter of the speaker is configured to be in contact with skin defining the ear canal when the ear-mounted apparatus is inserted into the ear canal.

5. The system according to claim 4, wherein the microphone is adjacent to the speaker and not to the outer portion, and is configured to extend further into the ear canal than the speaker when the ear-mounted apparatus is inserted into the ear canal.

6. The system according to claim 5, wherein the microphone is configured to not be in contact with the skin defining the ear canal when the ear-mounted apparatus is inserted into the ear canal.

7. A state estimation method comprising:
outputting, by a speaker of an ear-mounted apparatus of a system at least partially inserted into an ear canal of a body, a first acoustic signal into the ear canal of the body;
detecting, by a microphone of the ear-mounted apparatus, a second acoustic signal produced by the first acoustic signal echoing inside the body;
generating, by at least one processor of a state estimation apparatus of the system executing instructions stored on at least one memory of the state estimation apparatus, acoustic characteristic information indicating an acoustic characteristic, using the first acoustic signal output to an ear canal of a body and the second acoustic signal produced by the first acoustic signal echoing inside the body;
generating, by the at least one processor executing the instructions, resonant frequency information indicating resonant frequencies, or spectral shape information indicating a spectral shape, using the acoustic characteristic information; and
estimating, by the at least one processor executing the instructions, a state of a vocal tract of the body and a state of a respiratory tract of the body, using the generated resonant frequency information or spectral shape information,
wherein each of the state of the vocal tract and the state of the respiratory tract are at least one or more of is any one or any one or more of:
  a state indicating whether a mouth of the body is open or closed,
  a state indicating whether vocal cords of the body are open or closed,
  a state indicating a place of articulation of a tongue of the body, and
  a state indicating a type of breathing of the body.

8. A non-transitory computer readable recording medium storing instructions executable by at least one processor of a state estimation apparatus to perform processing comprising: outputting, to a speaker of an ear-mounted apparatus of the system configured to be at least partially inserted into an ear canal of a body, a first acoustic signal to output into the ear canal of the body;
inputting, from a microphone of the ear-mounted apparatus, a second acoustic signal produced by the first acoustic signal echoing inside the body and detected by the microphone;
generating acoustic characteristic information indicating an acoustic characteristic, using the first acoustic signal output to an ear canal of a body and the second acoustic signal produced by the first acoustic signal echoing inside the body;
generating resonant frequency information indicating resonant frequencies, or spectral shape information indicating a spectral shape, using the acoustic characteristic information; and
estimating a state of a vocal tract of the body and a state of a respiratory tract of the body, using the generated resonant frequency information or spectral shape information,
wherein each of the state of the vocal tract and the state of the respiratory tract are at least one or more of is any one or any one or more of:
  a state indicating whether a mouth of the body is open or closed,
  a state indicating whether vocal cords of the body are open or closed,
  a state indicating a place of articulation of a tongue of the body, and
  a state indicating a type of breathing of the body.

* * * * *